US010341339B2

(12) United States Patent
Laine et al.

(10) Patent No.: US 10,341,339 B2
(45) Date of Patent: Jul. 2, 2019

(54) TECHNIQUES FOR HEARABLE AUTHENTICATION

(71) Applicant: HARMAN INTERNATIONAL INDUSTRIES, INC., Stamford, CT (US)

(72) Inventors: Heikki Laine, Pittstown, NJ (US); Donald Joseph Butts, Westport, CT (US)

(73) Assignee: HARMAN INTERNATIONAL INDUSTRIES, INCORPORATED, Stamford, CT (US)

( * ) Notice: Subject to any disclaimer, the term of this patent is extended or adjusted under 35 U.S.C. 154(b) by 190 days.

(21) Appl. No.: 14/919,555

(22) Filed: Oct. 21, 2015

(65) Prior Publication Data

US 2017/0118204 A1    Apr. 27, 2017

(51) Int. Cl.
| | |
|---|---|
| H04L 29/06 | (2006.01) |
| H04W 12/06 | (2009.01) |
| A61B 5/01 | (2006.01) |
| A61B 5/0205 | (2006.01) |
| A61B 5/0484 | (2006.01) |

(Continued)

(52) U.S. Cl.
CPC ........... H04L 63/0861 (2013.01); A61B 5/01 (2013.01); A61B 5/0205 (2013.01); A61B 5/04845 (2013.01); A61B 5/117 (2013.01); A61B 5/6817 (2013.01); A61B 7/04 (2013.01); H04L 63/10 (2013.01); H04W 12/06 (2013.01); *A61B 5/053* (2013.01); *A61B 2503/12* (2013.01); *H04W 84/12* (2013.01)

(58) Field of Classification Search
CPC ....... H04L 63/0861; H04L 63/10; A61B 5/01; A61B 5/04845; A61B 7/04; A61B 5/0205; A61B 5/6817; A61B 5/117; A61B 5/053; A61B 2503/12; H04W 12/06
USPC .............................................................. 726/7
See application file for complete search history.

(56) References Cited

U.S. PATENT DOCUMENTS

| | | |
|---|---|---|
| 5,577,981 A | 11/1996 | Jarvik |
| 5,844,674 A | 12/1998 | Sieben |

(Continued)

FOREIGN PATENT DOCUMENTS

CA    2917708 A1    1/2015

OTHER PUBLICATIONS

Extended European Search Report Application No. 16188985.2 dated Mar. 10, 2017.

(Continued)

*Primary Examiner* — Lynn D Feild
*Assistant Examiner* — Abdullah Almamun
(74) *Attorney, Agent, or Firm* — Artegis Law Group, LLP

(57) ABSTRACT

The various embodiments set forth an apparatus comprising an earpiece, a sensor configured to measure an inherent attribute associated with a user, a wireless transceiver configured to communicate with a wireless access point of a wireless communication network, and a controller. The controller is configured to establish authenticated access to the wireless communication network based on the inherent attribute associated with the user. An advantage of the disclosed embodiment is that a hearable device can conveniently authenticate user access to a network with enhanced security, based on one or more inherence factors that are measured by the hearable device.

18 Claims, 5 Drawing Sheets

(51) Int. Cl.
*A61B 5/117* (2016.01)
*A61B 5/00* (2006.01)
*A61B 7/04* (2006.01)
*A61B 5/053* (2006.01)
*H04W 84/12* (2009.01)

(56) References Cited

U.S. PATENT DOCUMENTS

| | | | |
|---|---|---|---|
| 6,891,467 B2* | 5/2005 | Perttunen | B60R 25/241 |
| | | | 180/287 |
| 7,664,961 B2* | 2/2010 | Blattner | G06F 3/03543 |
| | | | 713/182 |
| 7,780,080 B2* | 8/2010 | Owen | G06F 21/32 |
| | | | 235/375 |
| 9,058,473 B2* | 6/2015 | Navratil | G06F 21/32 |
| 9,805,534 B2* | 10/2017 | Ho | G07C 9/00571 |
| 2005/0043646 A1* | 2/2005 | Viirre | A61B 5/0482 |
| | | | 600/545 |
| 2011/0314530 A1 | 12/2011 | Donaldson | |
| 2014/0020089 A1* | 1/2014 | Perini, II | G06F 21/32 |
| | | | 726/19 |
| 2014/0272915 A1 | 9/2014 | Higashino et al. | |
| 2015/0028996 A1* | 1/2015 | Agrafioti | G06F 21/40 |
| | | | 340/5.82 |
| 2015/0172832 A1 | 6/2015 | Sharpe et al. | |
| 2015/0347734 A1* | 12/2015 | Beigi | G06F 21/32 |
| | | | 713/155 |
| 2016/0008206 A1 | 1/2016 | Devanaboyina | |

OTHER PUBLICATIONS

"Galvanic vestibular stimulation", Wikipedia, 2 pages, https://en.wikipedia.org/wiki/Galvanic_vestibular_stimulation.

Hemmert, et al., "Take me by the Hand: Haptic Compasses in Mobile Devices through Shape Change and Weight Shift", Proceedings: NordiCHI 2010, Oct. 16-20, 2010, 4 pages.

Hemmert, et al., "Weight-Shifting Mobiles: Two-Dimensional Gravitational Displays in Mobile Phones", CHI 2010, Media Showcase Session 3, Apr. 10-15, 2010, 5 pages.

Kojima, et al., "Pull-Navi A novel tactile navigation interface by pulling the ears", SIGGRAPH '09 ACM SIGGRAPH 2009 Emerging Technologies Article No. 19, Aug. 3-7, 2009, 1 page.

Maeda, et al., "Shaking the World: Galvanic Vestibular Stimulation As a Novel Sensation Interface", SIGGRAPH '05 ACM SIGGRAPH 2005 Emerging Technologies Article No. 17, Jul. 31-Aug. 4, 2005, 1 page.

Non-final Office Action for U.S. Appl. No. 14/954,597, dated Nov. 4, 2016, 10 pages.

International Search Report for Application No. PCT/US2016/056421, dated Nov. 15, 2016, 10 pages.

Non-final Office Action for U.S. Appl. No. 14/954,597 dated Nov. 4, 2016.

* cited by examiner

TECHNIQUES FOR HEARABLE AUTHENTICATION

BACKGROUND

Field of the Various Embodiments

The various embodiments relate generally to hearable electronic devices and, more specifically, to techniques for hearable authentication.

Description of the Related Art

It has become common practice for individual consumers to use telecommunications systems for conducting financial transactions, consumer-based transactions, and other types of transactions involving the use of sensitive information. For example, wireless communication devices, either alone or in conjunction with the Internet, are frequently used for point-of-sale (POS) and on-line transactions, such as banking, retail, and other similar transactions, where credit card information, debit card information, and/or other types of account information is transmitted between or among devices. In addition, wireless communication devices, more generally, are increasingly employed for accessing various networks, other wireless devices, and the like, as part of more routine day-to-day activities. However, such devices, and the access codes associated with such devices, are routinely exposed to potentially malicious or otherwise unauthorized users, which can compromise the security of any network accessible by these devices. Such malicious and unauthorized users are becoming more and more aggressive in trying to exploit any weaknesses in the security of networked devices or the networks associated with those devices. Consequently, developing robust security and authentication procedures for wireless communication devices has become all the more important.

As an example, smart phones with two-factor authentication can be compromised quite easily. First, when a user authorizes access to a wireless network by entering a personal identification number (PIN) via a smartphone, the PIN may be intercepted electronically, or simply procured by someone watching and memorizing the PIN during PIN entry. Either way, the knowledge authentication factor associated with the smartphone (i.e., the PIN), can be readily obtained by a malicious user. Similarly, the possession authentication factor associated with the smartphone (i.e., physical control of the smartphone) can be obtained by a malicious user by simply stealing or gaining temporary electronic access to the smartphone.

In sum, the convenience afforded by using a wireless communication device to perform secure transactions and to access networks and other devices can be easily outweighed by the added security risks associated with using wireless communication device for these purposes. Accordingly, what would be useful are techniques for more securely accessing networks via wireless communication devices.

SUMMARY

The various embodiments set forth an apparatus comprising an earpiece, a sensor configured to measure an inherent attribute associated with a user, a wireless transceiver configured to communicate with a wireless access point of a wireless communication network, and a controller. The controller is configured to establish authenticated access to the wireless communication network based on the inherent attribute associated with the user.

At least one advantage of the disclosed embodiments is that a hearable device can conveniently authenticate user access to a network with enhanced security, based on one or more inherence factors that are measured by the hearable device.

BRIEF DESCRIPTION OF THE SEVERAL VIEWS OF THE DRAWINGS

So that the manner in which the above recited features of the various embodiments can be understood in detail, a more particular description of the various embodiments, briefly summarized above, may be had by reference to embodiments, some of which are illustrated in the appended drawings. It is to be noted, however, that the appended drawings illustrate only typical embodiments and are therefore not to be considered limiting of its scope, for the various embodiments may admit to other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

Figure 1:
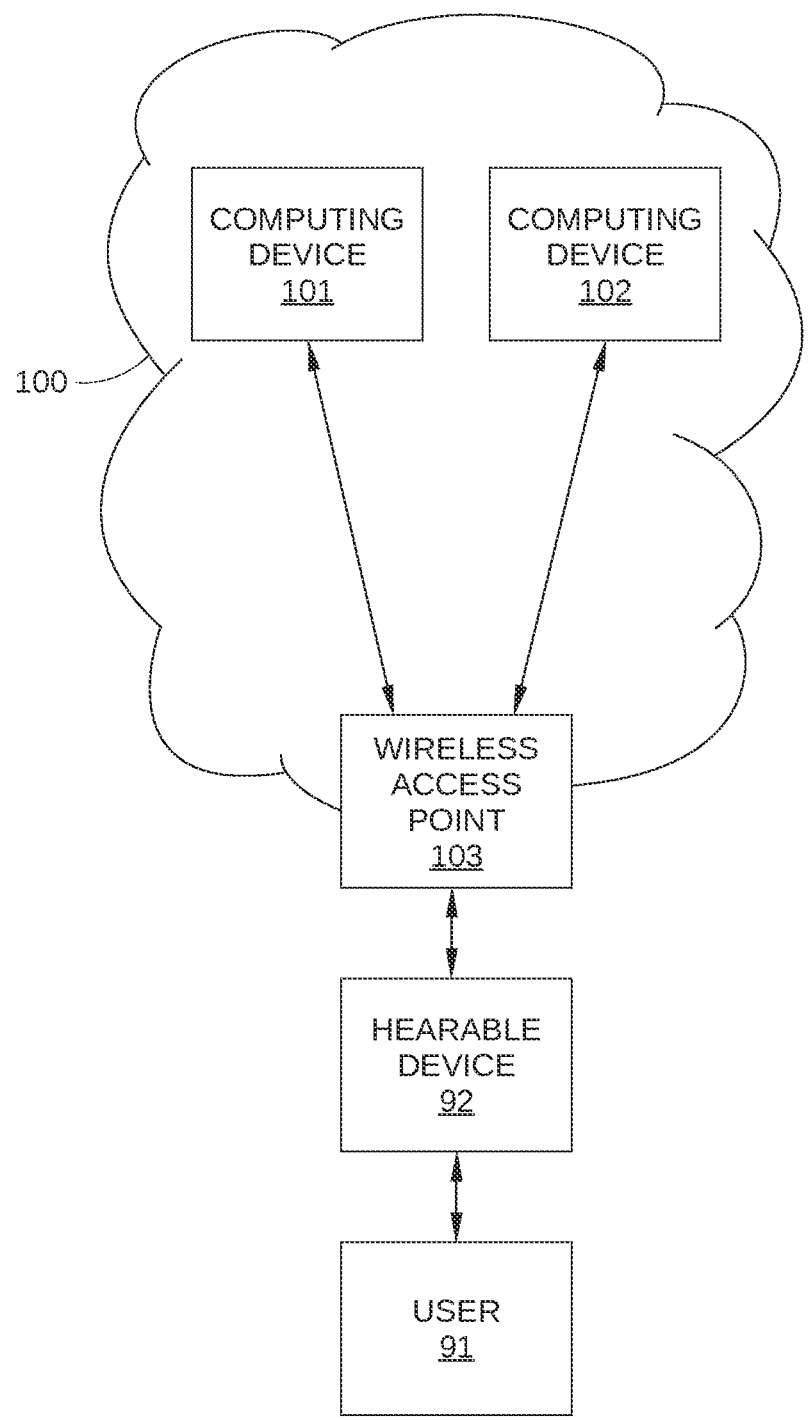
FIG. 1 is a schematic diagram illustrating a wireless communication network configured to implement one or more aspects of the various embodiments.

FIG. 1 is a schematic diagram illustrating a wireless communication network 100, configured to implement one or more aspects of the various embodiments. Also shown in FIG. 1 is a user 91 and a hearable device 92 configured to authenticate access to wireless communication network 100 by user 91. Wireless communication network 100 may include, without limitation, computing devices 101 and 102 and a wireless access point 103. Wireless communication network 100 may be any technically feasible type of communications network that allows data to be exchanged between computing device 101, computing device 102, and other entities or devices, such as a web server or another networked computing device. For example, wireless communication network 100 may include a wide area network (WAN), a local area network (LAN), a wireless (WiFi) network, and/or the Internet, among others. In some embodiments, wireless communication network 100 may include multiple network entry points, but for clarity, only a single wireless access point 103 is depicted in FIG. 1.

Each of computing devices 101 and 102 may be any stand-alone computing device operable to communicate via wireless communication network 100, including, without limitation, a desktop computer, a laptop computer, a smart phone, a personal digital assistant (PDA), a tablet computer, an automated teller machine or point-of-sale device configured with smartphone authentication, and the like. Alternatively or additionally, one or more of computing devices 101 and 102 may be a computing device operable to communicate via wireless communication network 100 and incorporated into an electronic device, consumer product, vehicle, or other apparatus, including, without limitation, a video game console, a set top console, a digital video recorder, a digital video disk player, a vehicle information system for a particular vehicle, and the like.

Wireless access point 103 is configured to authenticate access requests and provide authenticated access to wireless communication network 100. In some embodiments, wireless access point 103 may be a software interface associated with a specific computing device within wireless communication network 100, such as computing device 101 or 102. Alternatively, wireless access point 103 may be an interface associated with a stand-alone computing device within wireless communication network 100, such as a gateway computer or the like. Thus, when user 91 attempts to access a particular computing device within wireless communication network 100 via hearable device 92, wireless access point 103 may operate as part of the particular computing device, or may be a separate entity that authorizes user access to the particular computer device. In operation, wireless access point 103 may serve as an authorization entity for access to wireless communication network 100, receiving and authorizing requests to access computing device 101 and/or computing device 102, for example from hearable device 92.

Hearable device 92 may be any wearable electronic device that includes an earpiece or other audio interface configured for insertion in the ear canal of a user. For example, hearable device 92 may include an earpiece or audio earbud that is Bluetooth®-capable. In such embodiments, the earpiece or audio earbud may be configured to wirelessly communicate with an external computing device, such as a smartwatch, a smartphone, an electronic table, and the like. The external computing device may provide more processing power, greater memory, and/or a more ergonomic user interface than may be practicable in an earpiece or earbud form-factor. Alternatively or additionally, the earpiece or earbud may be configured with a wired connection to the external computing device. One embodiment of hearable device 92 is illustrated in FIGS. 2A-2C.

Figure 2A:
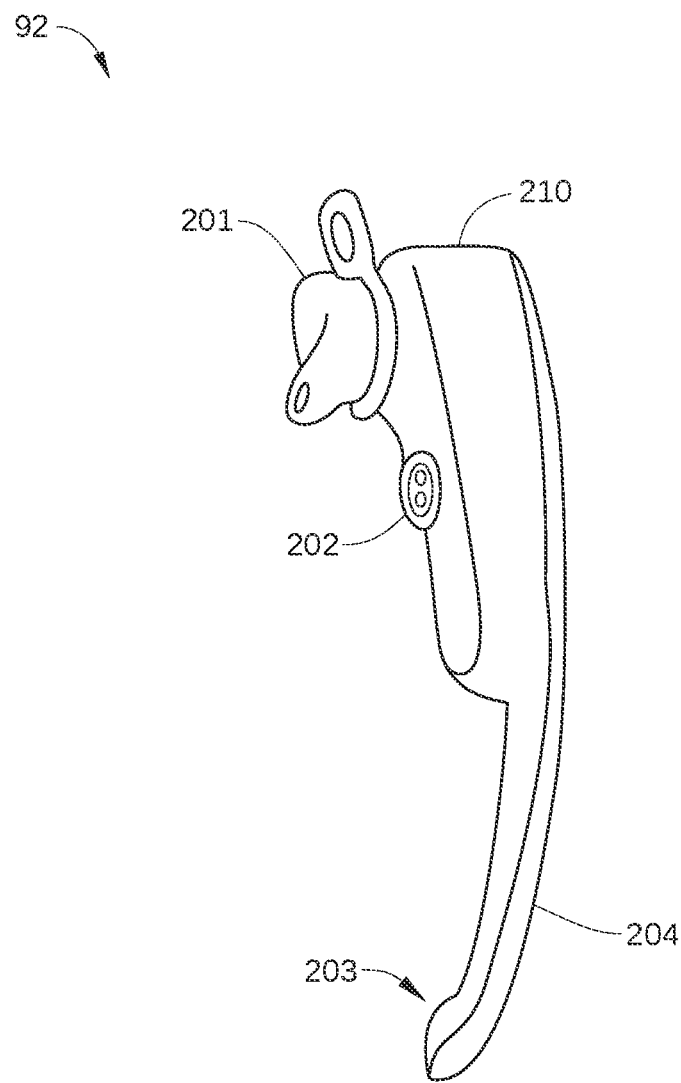
FIG. 2A is a schematic diagram of the hearable device of FIG. 1, according to the various embodiments.

FIG. 2A is a schematic diagram of hearable device 92, configured according to the various embodiments. Hearable device 92 may include, without limitation, an earpiece 201, a connection terminal 202, and a microphone 203 that is disposed on an end of a mic boom 204, all coupled to a body 210. FIG. 2B is a more detailed block diagram of earpiece 201, configured according to the various embodiments, and FIG. 2C is a more detailed block diagram of body 210, configured according to the various embodiments.

Figure 2B:
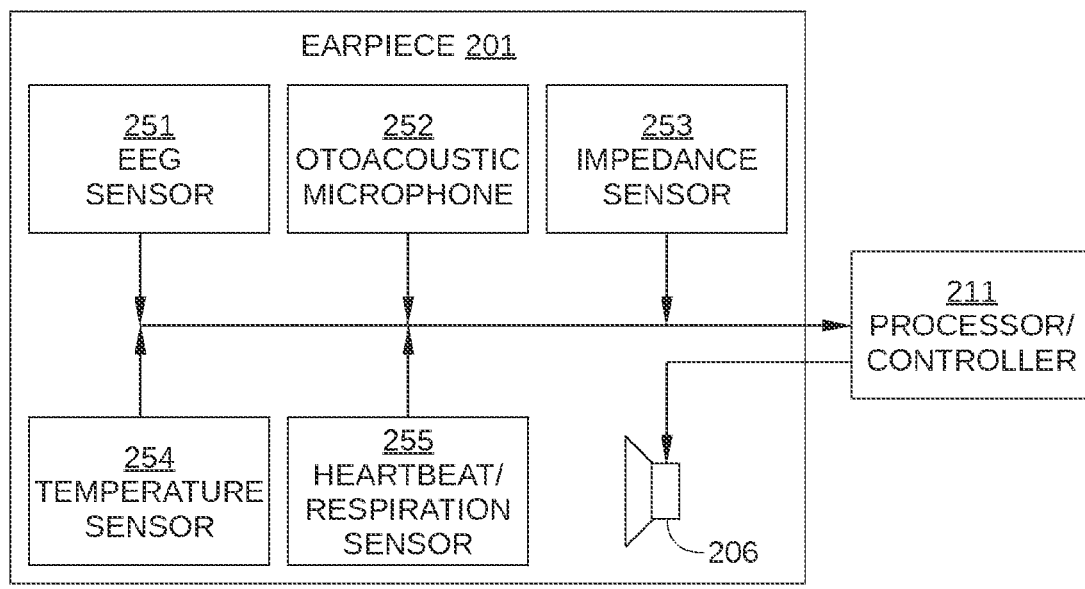
FIG. 2B is a more detailed block diagram of the earpiece of FIG. 2A, according to the various embodiments.
Figure 2C:
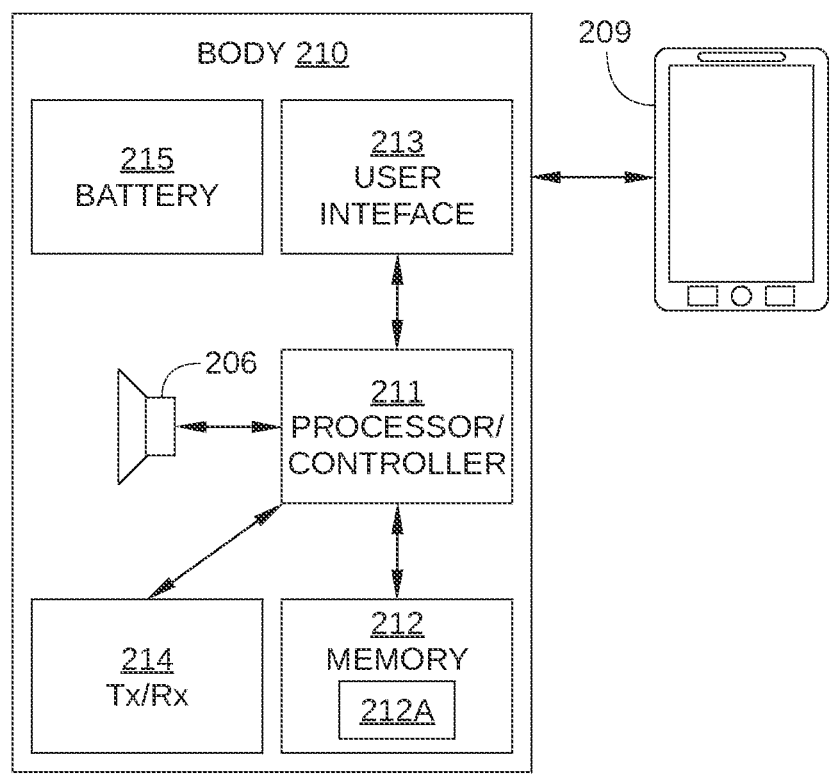
FIG. 2C is a more detailed block diagram of the body of FIG. 2A, according to the various embodiments.

As shown in FIGS. 2A and 2B, earpiece 201 is an earpiece configured for insertion at least partially in the ear canal of a user. In some embodiments, earpiece 201 is a custom-fit earpiece specifically designed to conform to at least a portion of the ear canal of the particular user, thereby substantially isolating the ear canal of the user acoustically from the surroundings. For example, earpiece 201 may be formed based on a laser scan, digital image or other three-dimensional scan, or physical mold of the ear canal of the particular user. Consequently, a suitable contact patch is generally formed between earpiece 201 and the ear canal of a user when hearable device 92 is worn by the particular user for whom earpiece 201 is constructed. Earpiece 201 may include, without limitation, one or more of an electroencephalogram (EEG) sensor 251, an otoacoustic microphone 252, an impedance sensor 253, a temperature sensor 254, and a heartbeat/respiration sensor 255, all of which are coupled to a processor 211 (described below in conjunction with FIG. 2C). In some embodiments, a loudspeaker 206 may also be included in earpiece 201, whereas in other embodiments, loudspeaker 206 may be disposed in body 210 of hearable device 92.

EEG sensor 251 may include any technically feasible sensor or sensors operable to non-invasively detect electrical activity of a user's brain, particularity in response to an acoustic trigger generated by loudspeaker 206. For example, in some embodiments, EEG sensor 251 may include one or more electrodes disposed on a surface of earpiece 201 and configured to contact one or more surfaces of the ear canal of a specific user when hearable device 92 is worn by the particular user for whom earpiece 201 is constructed. Such electrodes may be configured to measure voltage fluctuations resulting from ionic current within the neurons of the user's brain in response to the acoustic trigger generated by loudspeaker 206. Because the spontaneous electrical activity (i.e. neural oscillations) are unique to an individual, the signals detected by EEG sensor 251 may be considered a biometric signature, similar to a fingerprint. Consequently, in some embodiments, such detected signals may be employed as an inherence factor for secure authentication, i.e., an inherent attribute of a user, such as something unique that a user is or does. The EEG signature associated with the authorized user may be stored locally in hearable device 92, for example in a one-time programmable memory 212A (described below in conjunction with FIG. 2C), and/or in wireless communication network 100, for example in wireless access point 103.

Otoacoustic microphone 252 may include any technically feasible sensor or sensors operable to reliably detect otoacoustic emission (OAE) from the ear of the user, particularity in response to an acoustic trigger generated by loudspeaker 206. OAE is a sound that is emitted from within the inner ear, and evoked OAEs (EOAEs) are sounds emitted from within the inner ear when sound waves are incident on the ear. In some embodiments, otoacoustic microphone 252 is configured to detect EOAEs that are stimulated by an acoustic trigger, typically generated by loudspeaker 206. The outer hair cells of the inner ear function as actuators that add energy to incoming sound waves, for example the sound waves associated with the acoustic trigger generated by loudspeaker 206. Recent studies have validated that EOAEs may be used as a biometric signature, since EOAEs are unique for every person. Thus, in some embodiments, such detected signals may be employed as an inherence factor for secure authentication. The otoacoustic signature associated with the authorized user may be stored locally in hearable device 92, for example in one-time programmable memory 212A, and/or in wireless communication network 100, for example in wireless access point 103.

Impedance sensor 253 may include any technically feasible sensor or sensors operable to reliably measure a "contact impedance," i.e., the electrical impedance of a contact patch between earpiece 201 and one or more surfaces of the ear canal of user 91. Because contact impedance is highly dependent on the fit of earpiece 201 with the ear canal in which earpiece 201 is fitted, contact impedance detected by impedance sensor 253 may be employed as an inherence factor associated with the current user. Specifically, contact impedance exceeding a specific threshold indicates that earpiece 201 is either inserted incorrectly in the ear canal of the user for whom earpiece 201 is constructed, or is inserted in the ear canal of an unauthorized user, i.e., any user that is not the user for whom earpiece 201 is constructed. Thus, in some embodiments, the inability of a user to position earpiece 201 in such a way that contact impedance associated with earpiece 201 is less than a threshold value indicates that an unauthorized user is attempting to use hearable device 92. Consequently, in some embodiments, contact impedance, as measured by impedance sensor 253, may be employed as an inherence factor for secure authentication. In some embodiments, contact impedance may be employed by hearable device 92 to indicate that the authorized user of hearable device 92 has not properly seated earpiece 201 in the ear canal, and/or that earpiece 201 has been removed by a user. The contact impedance associated with the authorized user may be stored locally in hearable device 92, for example in one-time programmable memory 212A, and/or in wireless communication network 100, for example in wireless access point 103.

Temperature sensor 254 may include any technically feasible sensor or sensors operable to measure a body temperature of user 91, such as a thermistor or a thermocouple. The body temperature measured in the ear canal of a user by temperature sensor 254 may, in some embodiments, be employed to confirm that a user is wearing hearable device 92. Thus, in some embodiments, the current body temperature may be used as an inherence security factor for authentication of the user of hearable device 92. For example, when a user attempts to access wireless communication network 100 in FIG. 1, authentication of the identity of the user may depend in part on the current body temperature measured by temperature sensor 254 to confirm that earpiece 201 has not been removed by a user.

Heartbeat/respiration sensor 255 may include any technically feasible sensor or sensors operable to monitor heartbeat and/or respiration rate of a user 91. In some embodiments, heartbeat/respiration sensor 255 may use audio input from otoacoustic microphone 252, whereas in other embodiments, heartbeat/respiration sensor 255 may include a dedicated microphone. Because heartbeat and respiration of each person is substantially unique, a heartbeat measured in the ear canal of a user by heartbeat/respiration sensor 254 may, in some embodiments, be employed to confirm that the user wearing hearable device 92 is the authorized user of hearable device 92. Thus, in some embodiments, a heartbeat signature may be used as an inherence security factor for authentication of the user of hearable device 92. For example, when a user attempts to access wireless communication network 100 in FIG. 1, authentication of the identity of the user may depend in part on whether the heartbeat signature measured by heartbeat/respiration sensor 255 matches a heartbeat signature associated with the authorized user of hearable device 92. The heartbeat signature associated with the authorized user may be stored locally in hearable device 92, for example in one-time programmable memory 212A, and/or in wireless communication network 100, for example in wireless access point 103. In some embodiments, the absence of heartbeat or respiration may be employed by hearable device 92 to indicate that earpiece 201 has been removed by a user.

Connection terminal 202, shown in FIG. 2A, may be disposed on a side surface of body 210, and may include one or more connector plugs for charging hearable device 92 and/or for inputting external information to hearable device 92 via a wired connection (not shown). Microphone 203 may be disposed on an end of mic boom 204, and is configured for voice communication. Body 210, which is shown in FIGS. 2A and 2C, may house, without limitation, processor 211, a memory 212, a user interface 213, a transceiver (Tx/Rx) 214, and a battery 215. In some embodiments, loudspeaker 206 may also be disposed in body 210.

Processor 211 may be any suitable processor implemented as a central processing unit (CPU), an application-specific integrated circuit (ASIC), a field programmable gate array (FPGA), any other type of processing unit, or a combination of different processing units. In general, processor 211 may be any technically feasible hardware unit capable of processing data and/or executing software applications to facilitate operation of hearable device 92 as described herein. Thus, in some embodiments, processor 211 may be configured as a controller for hearable device 92.

Memory 212 may include volatile memory, such as a random access memory (RAM) module, and non-volatile memory, such as a flash memory unit, a read-only memory (ROM), or any other type of memory unit or combination thereof suitable for use in hearable device 92. Memory 212 is configured to store any software programs, operating system, drivers, and the like, that facilitate operation of hearable device 92. In some embodiments, memory 212 includes a one-time programmable memory 212A, configured to store one or more inherence factors associated with the authorized user of hearable device 92. In such embodiments, only a single authorized user is typically associated with hearable device 92. However, in some embodiments, one-time programmable memory 212A may be configured to store one or more inherence factors associated with multiple authorized users of hearable device 92.

User interface 213 is configured to enable user inputs to hearable device 92, such as powering hearable device on and off, initiating and ending calls, changing volume, and the like. Thus, user interface 213 may include, without limitation, one or more mechanical (rocker, up-down, toggle) buttons or touch sensors disposed on an outer surface of housing 210. In some embodiments, user interface 213 may also be configured to communication with one or more display elements or devices. In some embodiments, such display elements or devices may be associated with an external computing device 209, such as an electronic tablet or smartphone operable to communicate with hearable device 92 and display content associated with operation of hearable device 92. For example, as part of a user authentication process, user interface 213 may be configured to facilitate the entry of a PIN via an application running on such an external computing device 209.

Transceiver 214 may be any technically feasible apparatus configured to provide a wireless communications link between hearable device 92 and network wireless access point 103. For example, but without limitation, wireless transceiver 130 may be a Bluetooth® access point. Alternatively or additionally, wireless transceiver 130 may be configured with cellular communication capability, satellite telephone communication capability, a wireless wide area network communication capability, or other types of communication capabilities that allow for communication with wireless communication network 100 and computing devices 101 and 102.

Battery 215 may be any suitable energy storage battery suitable for use in hearable device 92, is configured to provide power to hearable device 92 during operation, and is typically a rechargeable battery.

According to embodiments described herein, hearable device 92 is configured to enable a user to securely access a computing device within wireless communication network 100. Specifically, hearable device 92 enables such secure access by incorporating an inherence factor associated with the user into the authentication process. Hearable device 92 may employ the inherence factor either alone or in conjunction with one or more other authorization factors, such as a knowledge factor (e.g., knowledge of a PIN or password) and/or a possession factor (e.g., possession of a physical fob, key, and/or hearable device 92 itself). Suitable inherence factors employed by hearable device 92 may include, without limitation, an EEG reading or signature measured by EEG sensor 251 or an otoacoustic signature measured by otoacoustic microphone 252. In addition to or in lieu of these biometric signatures, hearable device 92 may employ one or more other inherence factors as an inherence factor during an authentication process, such as earpiece fit, measured by impedance sensor 253, body temperature, measured by temperature sensor 254, or a heart beat signature, measured by heartbeat/respiration sensor 255. Any other suitable inherence factors not directly measured by a sensor in hearable device 92, such as fingerprint or retina imagery, may also be included in such an authentication process.

Thus, when the user of hearable device 92 enters the wireless signal range of wireless communication network 100, hearable device 92 and wireless access point 103 establish a secure connection based on at least one inherence factor associated with the user of hearable device 92 and measured by hearable device 92. In this way, a secure connection is established between hearable device 92 and wireless communication network 100 without the need for manual entry of a PIN or possession of a security fob by the user of hearable device 92. Instead, the secure connection may be established transparently. For example, in embodiments in which wireless communication network 100 is associated with a vehicle or a home network, a physical key is not needed for entry to the vehicle or home. This is because hearable device 92 determines the identity of a user by measuring one or more of the inherence factors described above, and either provides the one or more inherence factors to the network as part of an authentication process or simply notifies the network that the user wearing hearable device 92 is an authenticated user.

For example, in some embodiments, wireless communication network 100 may be as simple as a single computing device, such as computing device 101, and a single network entry point, such as wireless access point 103. In such an embodiment, computing device 101 may be associated with a vehicular infotainment system, a home network and entertainment system, or an individual apparatus, such as an electronic tablet, DVD player, and the like. Thus, when the user of hearable device 92 enters the wireless signal range of wireless communication network 100 (for example, the user approaches the vehicle associated with wireless communication network 100), wireless access point 103 may query hearable device 92 whether user 91 is an authenticated user. Alternatively, wireless access point 103 may query hearable device directly for one or more specific inherence factors to authenticate user 91. As noted, each such inherence factor is based on an inherent attribute of the user of hearable device 92 that hearable device 92 is configured to detect, i.e., an EEG signature, an otoacoustic signature, earpiece fit/impedance, heart beat signature, and the like. Hearable device 92 then measures the appropriate inherent attribute of the user, provides the inherence factor based thereon to wireless access point 103, and receives access to wireless communication network 100 when the inherence factor provided is determined to be correct, thereby completing the authentication process.

In some embodiments, when hearable device 92 (and by extension user 91) receives access to wireless communication network 100, user 91 may then access communication network as a typical network user, and access the Internet, transfer data to and/or from computing devices 101 and/or 102, etc. Alternatively or additionally, in other embodiments, when hearable device 92 and user 91 receive access to wireless communication network 100, one or more automated processes may occur. For example, when computing device 101 is associated with a vehicle, computing device 101 may automatically initiate one or more vehicle-specific actions, such as unlocking and/or starting the vehicle, powering up an infotainment system associated with the vehicle, and downloading and/or implementing personalized settings for vehicle systems associated with user 91 (e.g., radio settings, mirror positions, seat adjustments, audio system settings, environmental control settings, etc.). In some embodiments, the personalized settings may be downloaded from cloud storage or from hearable device 92, via wireless communication network 100. Alternatively or additionally, such personalized settings may be stored in computing device 101. In another example, when computing device 101 is associated with a home network and entertainment system, computing device 101 may automatically initiate one or more home network-specific actions, such as deactivating a home security system, powering specific lights on or off, modifying heating and cooling setpoints, and the like.

Figure 3:
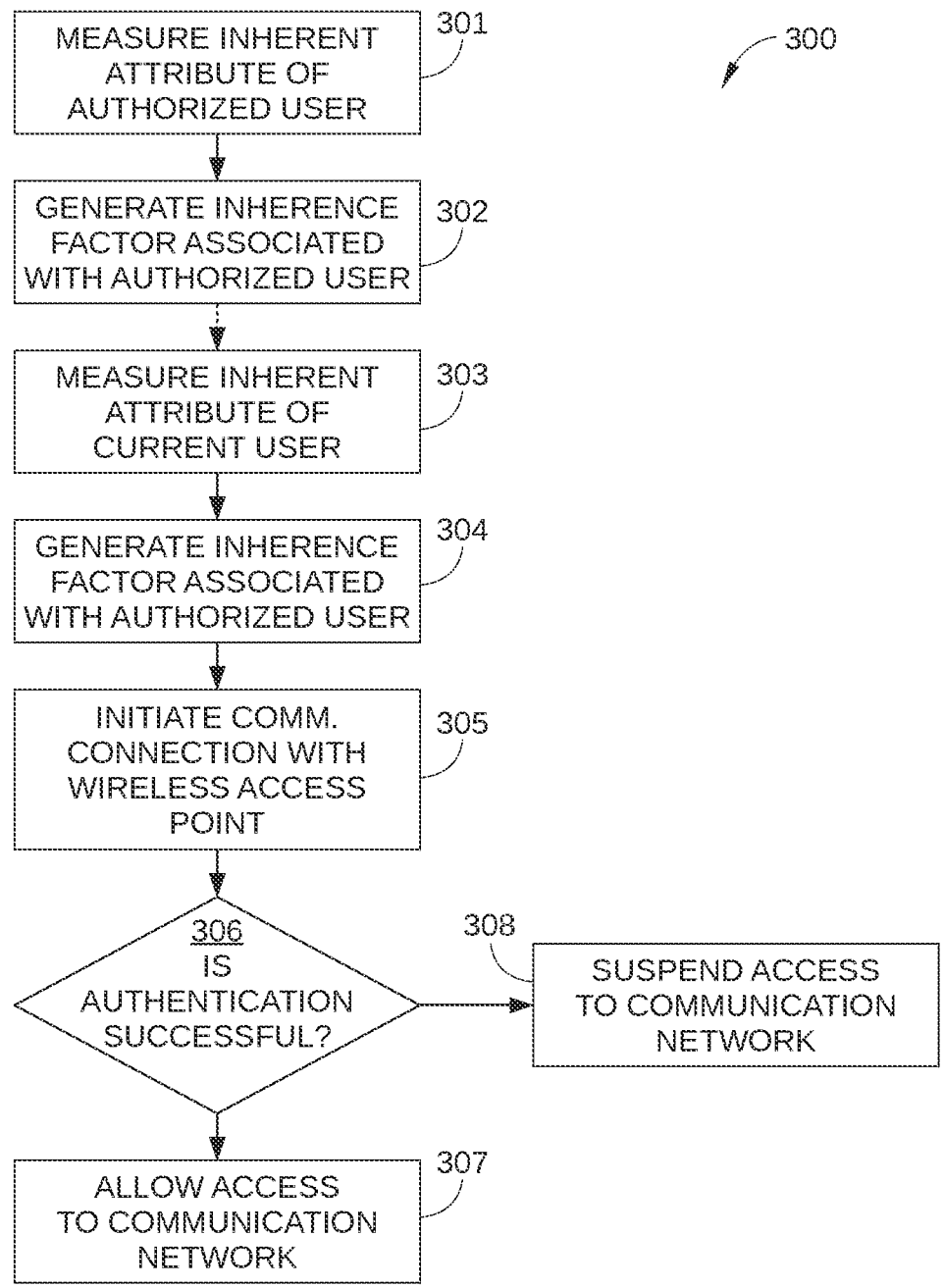
FIG. 3 sets forth a flowchart of method steps for securely accessing a wireless network, according to the various embodiments.

FIG. 3 sets forth a flowchart of method steps for securely accessing a wireless network, according to the various embodiments. Although the method steps are described with respect to the systems of FIGS. 1-2C, persons skilled in the art will understand that any system configured to perform the method steps, in any order, falls within the scope of the various embodiments.

As shown, a method 300 begins at step 301, in which hearable device 92 measures one or more inherent attributes associated with an authorized user of hearable device 92, such as user 91. The one or more inherent attributes may include, without limitation, an EEG signature, an otoacoustic signature, earpiece fit or impedance, or a heart beat signature, among others. In some embodiments, measurement of the inherent attribute may involve generating an audio stimulus, for example via loudspeaker 206, and recording a response measured by a sensor included in earpiece 201. In other embodiments, the one or more inherent attributes may be measured without a triggering stimulus.

In step 302, hearable device 92 generates an inherence factor based on the inherent attributes measured in step 301, i.e., the unique value, function, or signature that is associated with the particular user for the inherent attribute. In addition, hearable device 92 stores the inherence factor so generated, either locally in one-time memory 212A, remotely in a computing device within wireless communication network 100, or both locally and remotely. In some embodiments, hearable device 92 is configured so that only a single authorized user may be associated with hearable device 92, and in such embodiments, one-time memory 212A is programmed accordingly. It is noted that steps 301 and 302 may be performed upon initial startup of hearable device 92, when user 91 is first established as the authorized user of hearable device 92.

In step 303, hearable device 92 measures an inherent attribute of the user currently wearing hearable device 92, for example via one or more sensors disposed within earpiece 201. As described above in step 301, measurement of the inherent attribute of the user currently wearing hearable device 92 may include generating an audio stimulus, for example via loudspeaker 206, and recording a response. In step 304, based on the inherent attribute measured in step 303, hearable device 92 generates an inherence factor associated with the current wearer of hearable device 92, i.e., the unique value, function, or signature that is associated with the current user for the inherent attribute.

In some embodiments, steps 303 and 304 are performed in response to a user powering on hearable device 92 and/or donning hearable device 92. In such embodiments, hearable device 92 is typically configured to determine whether the current wearer of hearable device 92 is the authorized user of hearable device 92, i.e., whether the current wearer of hearable device 92 is matched to hearable device 92. Thus, in such embodiments, the authentication functionality associated with providing secure access to wireless communication network 100 typically resides in hearable device 92. In such embodiments, the donning and removal of hearable device 92 may be detected by impedance sensor 253, temperature sensor 254, and/or heartbeat/respiration sensor 255.

Alternatively, in some embodiments, steps 303 and 304 are performed in response to hearable device 92 entering the wireless signal range of wireless communication network 100 and/or receiving a query from wireless access point 103 for an inherence factor associated with the current user of hearable device 92. For example, such a query may be received from wireless access point 103 in embodiments in which the inherence factor associated with the authorized user of hearable device 92 is not stored locally in hearable device 92, and is only stored remotely in a computing device within wireless communication network 100. Thus, in such embodiments, the authentication functionality associated with providing secure access to wireless communication network 100 typically resides in wireless access point 103.

In step 305, hearable device 92 initiates a communication connection with wireless access point 103, such as when user 91 enters the wireless signal range of wireless communication network 100 while wearing hearable device 92. For example, when wireless communication network 100 is associated with a vehicle information system for a particular vehicle, step 305 may take place when user 91 approaches the particular vehicle; when wireless communication network 100 is associated with a home network, step 305 may take place when user 91 approaches the home associated with the home network.

In step 306, an authentication process for hearable device 92 is performed with respect to wireless communication network 100. When the authentication process is successfully completed, i.e., hearable device 92 and user 91 is authenticated, method 300 proceeds to step 307; when the authentication process is not successfully completed, i.e., hearable device 92 or user 91 is not authenticated, method 300 proceeds to step 308.

In some embodiments, as part of the authentication process of step 306, hearable device 92 determines whether the current wearer of hearable device 92 is properly matched to hearable device 92. For example, hearable device 92 may compare the inherence factor generated in step 304 (i.e., the inherence factor generated for and associated with the current wearer of hearable device 92) to the inherence factor generated in step 302 (i.e., the inherence factor generated and stored for and associated with the authorized wearer of hearable device 92). When the inherence factor generated in step 304 is sufficiently similar to the inherence factor generated in step 302, hearable device 92 is considered to properly match the current wearer of hearable device 92, and hearable device 92 performs a conventional authentication process with wireless access point 103. Specifically, hearable device 92 may transmit a unique ID associated with hearable device 92 to wireless access point 103, wireless access point 103 looks up the unique ID in communications network 100, and grants access thereto when the unique ID transmitted is correct.

It is noted that in some embodiments, hearable device 92 may determine whether the current wearer of hearable device 92 is properly matched to hearable device 92 prior to the current wearer of wearing hearable device 92 entering the wireless signal range of wireless communication network 100 (step 305). For example, hearable device 92 may determine whether the current wearer of hearable device 92 is properly matched to hearable device 92 whenever a particular user powers up hearable device 92, or whenever a particular user dons hearable device 92, as detected by one or more sensors in earpiece 201.

In other embodiments, the authentication process for hearable device 92 may be largely performed by wireless access point 103. As noted above in steps 303 and 304, in such embodiments, wireless access point 103 may query hearable device 92 for an inherence factor associated with the current user of hearable device 92. In such embodiments, the inherence factor for the authorized user of hearable device 92 may only be stored remotely from hearable device 92, such as in wireless access point 103 or computing device 101. Thus, the authentication process performed by wireless access point 103 includes comparing the inherence factor for the authorized user of hearable device 92 to the inherence factor associated with the current wearer of hearable device 92 that is generated by hearable device 92 in step 304.

In step 307, which is performed in response to hearable device 92 and user 91 being successfully authenticated, wireless entry point 103 allows access to communications network 100. In step 308, which is performed in response to hearable device 92 or user 91 being unsuccessfully authenticated, wireless entry point 103 suspends access to communications network 100.

Thus, by implementation of method 300, secure access to a communication network is provided by hearable device 92 based on multiple-factor authentication. The multiple-factor authentication may include, without limitation, one or more inherence factors associated with the authorized user of hearable device 92 and measurable by hearable device 92 (e.g., an EEG signature, an otoacoustic signature, etc.), a possession factor (e.g., possession of hearable device 92), and any suitable knowledge factor (e.g., a PIN or password). In embodiments in which only inherence and possession factors are employed, multiple factor authentication can be performed transparently to the user. Consequently, a user can securely and conveniently access a communications network via hearable device 92 without the need for a PIN, a physical key or fob, and without the concern that mere possession of hearable device 92 may compromise the security of the communications network.

In sum, various embodiments set forth systems and techniques for securely accessing a computing device within a communication network via a hearable device. Advantageously, by authenticating a user of the hearable device based on one or more inherence factors that are measured by the hearable device, secure access to the communication network may be granted without a PIN or physical key or fob. A further advantage is that possession of the hearable device by an unauthorized user is insufficient to compromise the security of the communication network.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors or gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

The claimed invention is:

1. An apparatus comprising:
an earpiece;
a triggering device configured to generate an audio stimulus;
an electroencephalogram (EEG) sensor configured to measure an EEG signature of a user in response to the audio stimulus;
a wireless transceiver configured to communicate with a wireless access point of a wireless communication network, wherein the wireless communication network includes a device associated with a home network system of a home; and
a controller configured to establish authenticated access to the wireless communication network based on the EEG signature associated with the user;
wherein the device associated with the home network system is configured to, in response to the controller establishing authenticated access to the wireless communication network, perform one or more operations comprising at least one of deactivating a home security system of the home, powering one or more lights in the home on or off, and modifying at least one of a heating set point and a cooling set point in the home.

2. The apparatus of claim 1, wherein the sensor is disposed in the earpiece and is configured to contact a surface of an ear canal of the user.

3. The apparatus of claim 1, wherein the earpiece is configured to conform to at least a portion of an ear canal of a particular user.

4. The apparatus of claim 1, wherein the controller is configured to establish authenticated access to the wireless communication network by:
generating an inherence security factor based on the EEG signature of the user;
and authenticating the user based on the inherence security factor generated for the user.

5. The apparatus of claim 4, wherein the controller is configured to authenticate the user by comparing the inherence security factor generated for the user to an authorized inherence security factor.

6. The apparatus of claim 5, wherein the controller is further configured to: measure an EEG signature associated with an authorized user of the apparatus; and
generate the authorized inherence security factor based on the EEG signature associated with the authorized user of the apparatus.

7. The apparatus of claim 4, wherein the controller is configured to authenticate the user by transmitting the inherence security factor generated for the user to the wireless access point.

8. The apparatus of claim 1, wherein the controller is further configured to determine whether the user is wearing the apparatus prior to establishing authenticated access to the communication network.

9. A method for securely accessing a wireless communication network, the method comprising:
- generating an audio stimulus;
- measuring an electroencephalogram (EEG) signature associated with a user with an EEG sensor that is disposed in an earpiece and configured to contact a surface of an ear canal of the user, wherein the EEG sensor is configured to measure the EEG signature in response to the audio stimulus;
- generating an inherence security factor based on the EEG signature associated with the user,
- establishing authenticated access to the wireless communication network based on the inherence security factor, wherein the wireless communication network includes a device incorporated into a vehicle; and
- in response to establishing the authenticated access, performing, via the device, one or more operations comprising at least one of starting the vehicle, powering up an infotainment system associated with the vehicle, and implementing personalized settings of the user with a component of the vehicle.

10. The method of claim 9, wherein establishing authenticated access to the wireless communication network comprises communicating with a wireless access point of the wireless communication network via a wireless transceiver.

11. The method of claim 9, wherein establishing authenticated access to the wireless communication network comprises:
- authenticating the user based on the inherence security factor generated for the user.

12. The method of claim 11, further comprising authenticating the user by comparing the inherence security factor generated for the user to an authorized inherence security factor.

13. The method of claim 12, further comprising:
- measuring an EEG signature associated with an authorized user of the apparatus; and
- generating the authorized inherence security factor based on the EEG signature associated with the authorized user of the apparatus.

14. The method of claim 9, wherein the personalized settings comprise one or more of a radio setting, a mirror position, a seat adjustment, an audio system setting, and an environmental control setting.

15. The method of claim 9, wherein the wireless communication network is associated with a home network system of a home, and further comprising, in response to establishing the authenticated access, performing one or more operations comprising at least one of deactivating a home security system of the home, powering one or more lights in the home on or off, and modifying at least one of a heating set point and a cooling set point in the home.

16. A non-transitory computer readable medium storing instructions that, when executed by a processor, configure the processor to perform the steps of:
- generating an audio stimulus;
- measuring an electroencephalogram (EEG) signature associated with a user with an EEG sensor that is disposed in an earpiece and configured to contact a surface of an ear canal of the user, wherein the EEG sensor is configured to measure the EEG signature in response to the audio stimulus;
- establishing authenticated access to a wireless communication network based on the EEG signature associated with the user, wherein the wireless communication network includes a device incorporated into a vehicle; and
- in response to establishing the authenticated access, performing, via the device, one or more operations comprising at least one of starting the vehicle, powering up an infotainment system associated with the vehicle, and implementing personalized settings of the user with a component of the vehicle.

17. The non-transitory computer readable medium of claim 16, wherein establishing authenticated access to the wireless communication network comprises communicating with a wireless access point of the wireless communication network via a wireless transceiver.

18. The non-transitory computer readable medium of claim 16, further comprising the step of determining whether the user is wearing the apparatus prior to establishing authenticated access to the communication network.

* * * * *